(12) United States Patent
Umenei et al.

(10) Patent No.: US 11,083,810 B2
(45) Date of Patent: Aug. 10, 2021

(54) CONTROL PANEL HAVING UV DISINFECTION

(71) Applicant: GHSP, Inc., Grand Haven, MI (US)

(72) Inventors: Aghuinhue Umenei, Grand Rapids, MI (US); Robert W. Rossien, Muskegon, MI (US); Eric Bryant, Nunica, MI (US)

(73) Assignee: GHSP, Inc., Holland, MI (US)

( * ) Notice: Subject to any disclaimer, the term of this patent is extended or adjusted under 35 U.S.C. 154(b) by 31 days.

(21) Appl. No.: 16/736,691

(22) Filed: Jan. 7, 2020

(65) Prior Publication Data

US 2020/0215213 A1 Jul. 9, 2020

Related U.S. Application Data

(60) Provisional application No. 62/789,070, filed on Jan. 7, 2019, provisional application No. 62/789,060, filed on Jan. 7, 2019.

(51) Int. Cl.
*A61L 2/10* (2006.01)
*G06F 3/0484* (2013.01)

(52) U.S. Cl.
CPC .............. *A61L 2/10* (2013.01); *G06F 3/0484* (2013.01); *A61L 2209/12* (2013.01)

(58) Field of Classification Search
None
See application file for complete search history.

(56) References Cited

U.S. PATENT DOCUMENTS

| | | | | |
|---|---|---|---|---|
| 2008/0067417 | A1* | 3/2008 | Lane | A61L 2/24 250/455.11 |
| 2013/0093322 | A1* | 4/2013 | Borsuk | H05B 41/2806 315/39.51 |
| 2014/0225002 | A1* | 8/2014 | Blatchley, III | G06F 30/20 250/430 |
| 2017/0216472 | A1* | 8/2017 | Stibich | A61L 2/24 |
| 2019/0105415 | A1* | 4/2019 | Gross | A61L 2/10 |

FOREIGN PATENT DOCUMENTS

| | | | | |
|---|---|---|---|---|
| EP | 3043244 A1 * | 7/2016 | | A61L 2/10 |
| EP | 3043244 B1 * | 9/2019 | | G06F 3/041 |

* cited by examiner

*Primary Examiner* — Andrew Smyth
(74) *Attorney, Agent, or Firm* — Frank M. Scutch, III

(57) ABSTRACT

A control panel having a variety of potential applications that utilize ultraviolet-C (UV-C) light as a means of disinfection. In one embodiment, a human/machine interface (HMI) panel, such as a touchscreen or keypad uses a dynamically moveable multi-reflector assembly using UV-C light to disinfect its touch surfaces. The goal of integrating UV-C disinfection with an HMI works to provide a safe and effective dose of UV-C light to the panel's surface for the purpose of reducing the number of active pathogens.

18 Claims, 4 Drawing Sheets

CONTROL PANEL HAVING UV DISINFECTION

FIELD OF THE INVENTION

The present invention relates generally human-machine interfaces (HMIs) such as control panels for controlling electronic devices or the like.

BACKGROUND

Applying a safe and useful dose of Ultra-Violet C (UV-C) light to the surface of an HMI presents several problems. These include the need to maintain the safety of an operator, or anyone in the vicinity of the HMI. UV-C light in unsafe doses can present a hazard to the user and consequently excessive exposure must be avoided. Disinfection requires providing an effective dose of UV-C radiation to the entire surface of the HMI.

Many mounting scenarios preclude the mounting of a UV-C source orthogonally to the HMI's surface due to physical packaging reasons or aesthetic concerns which require the use of special materials that are compatible with UV-C. Most engineering materials absorb UV-C light instead of reflecting or transmitting it, and some materials can degrade in the presence of UV-C. Thus, solutions are needed to safely and efficiently disinfect the surface of control panels such as touchscreen LCDs as well as other electric devices which require the human touch.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
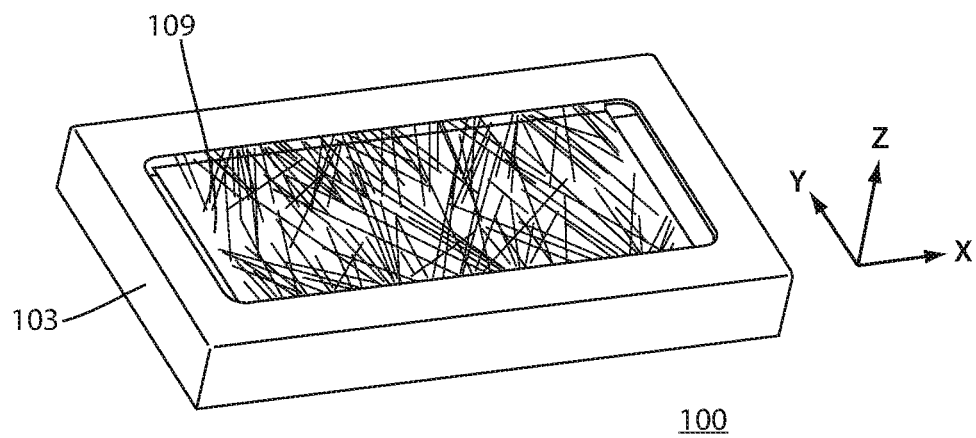
FIG. 1 is a perspective view of a control panel used in a human machine interface (HMI) in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a control panel having UV disinfection. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 2:
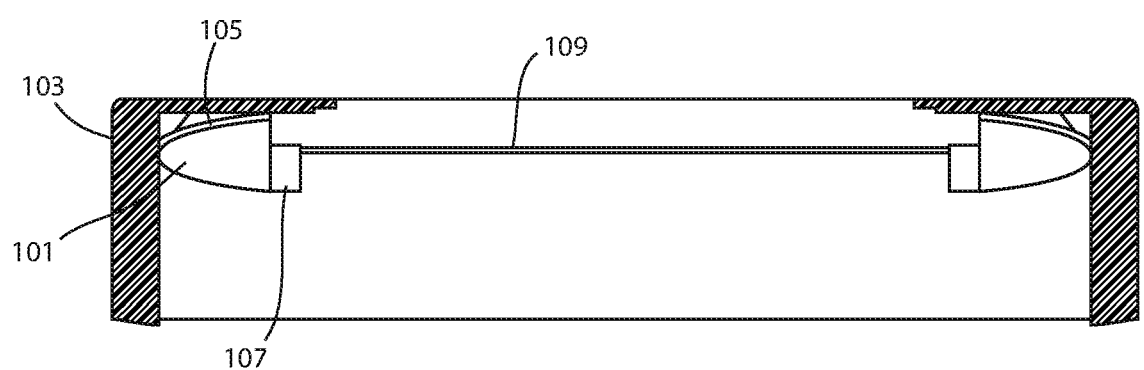
FIG. 2 is a side cross-sectional view of the control panel shown in FIG. 1.

FIG. 1 is a perspective view of a control panel used in a human machine interface (HMI) in accordance with an embodiment of the invention. FIG. 2 is a side cross-sectional view of the control panel shown in FIG. 1. With regard to both FIG. 1 and FIG. 2, the HMI control panel 100 is shown as used with a liquid crystal display (LCD) touch screen or the like. Those skilled in the art will recognize that a control panel might be used with any electric device and can include but is not limited to any panel using touch screen technology or other type of software touch control such as a keyboard or the like.

The control panel 100 uses one or more UV-C light source(s) 101 mounted under one or more side or edges of a housing such as an overlay or bezel 103. The bezel material is typically constructed of a UV transmissive material such as quartz or perfluoro-alkoxy plastic (PFA). The overlay 103 may also include a coating on its rear-facing surface to enhance reflectively. Materials are important when using UV-C since most engineering materials absorb UV-C light instead of reflecting or transmitting it, and some materials degrade in the presence of UV-C. Those skilled art will recognize that the light sources 101 may be many different technologies including but not limited to light emitting diode (LED).

As will be described herein, a primary reflector 105 and secondary reflector 107 are both moveable and used to direct the LED's UV-C emission across the surface 109 of an HMI such as a touch screen LCD or the like. FIG. 1 illustrates the UV-C emission from one or more dynamically moveable multi-reflector assemblies that can extend the light in each of X, Y and Z planes across the surface 109 of the touch screen for any desired time interval.

Figure 3A:
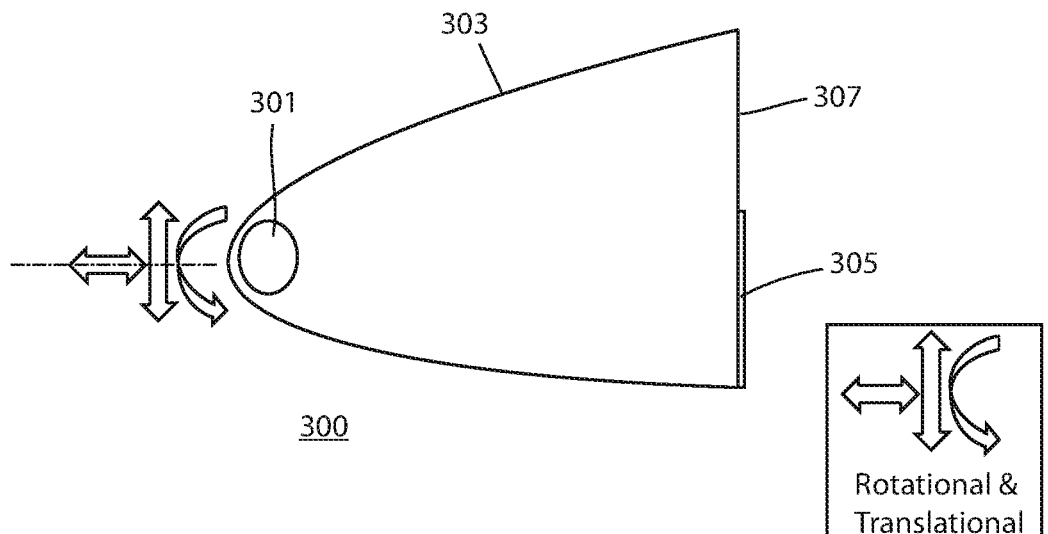
FIG. 3A is side view illustrating a UV-C light source and dynamic multi-reflector assembly in accordance with the invention.
Figure 3B:
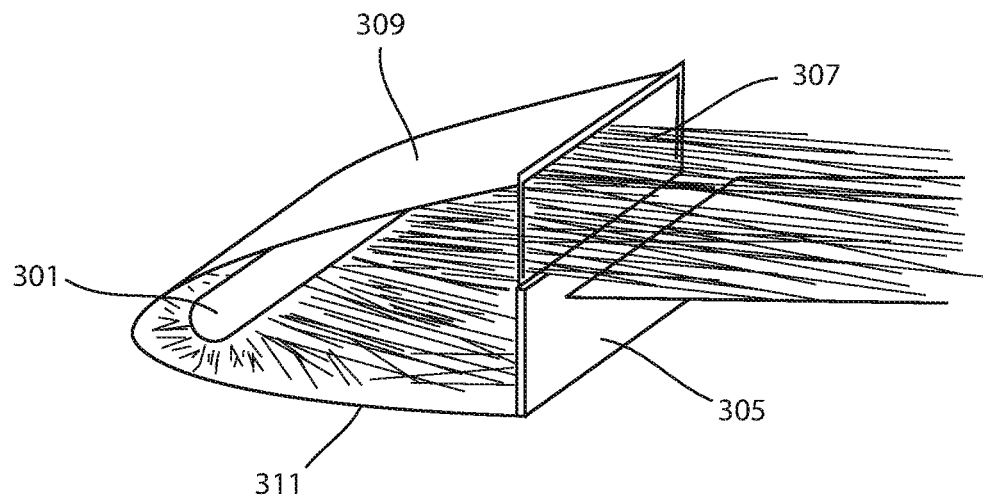
FIG. 3B is a perspective view of the dynamic multi-reflector assembly in operation.

FIG. 3A is side view illustrating a UV-C light source and dynamic multi-reflector assembly in accordance with an embodiment of the invention. FIG. 3B is a perspective view of the dynamic multi-reflector assembly in operation. With regard to both FIG. 3A and FIG. 3B, the he dynamic multi-reflector assembly 300 include a UV light source 301 that is positioned at the back or rear of a primary reflector 303. The primary reflector 303 is substantially U-shaped so the UV light source is typically positioned at the center or back of the U configuration between an upper and lower reflector. In another embodiment, the primary reflector may be a parabola type shape.

A secondary reflector 305, is substantially flat in shape, and is positioned, forward and substantially orthogonally to the light source 301. In this embodiment, the secondary light source is at some predetermined distance from light source 301 and configured below its central axis of emission. The secondary reflector 305 is smaller in size than the opening of the primary reflector such that light escapes only from above the secondary reflector. This enables the secondary reflector 303 to reflect light toward the primary reflector 301 where the primary reflector 303 reflects light out of its front opening. A novel attribute of this design is that the reflector movement mechanism is both rotational and transactional. Thus, the primary reflector 301 and the secondary reflector 303 and be independently rotated and/or move to provide the desired amount or dose of light emission though a bezel aperture 307. The dynamic multi-reflector assembly 300 enables the dose of UV-C light to be precisely controlled for the optimum amount of pathogen disinfection. Thus, the dynamic multi-reflector assembly 300 offers dynamic movability since both the light source and reflectors can be moved to direct light emission to a specific location.

Figure 4:
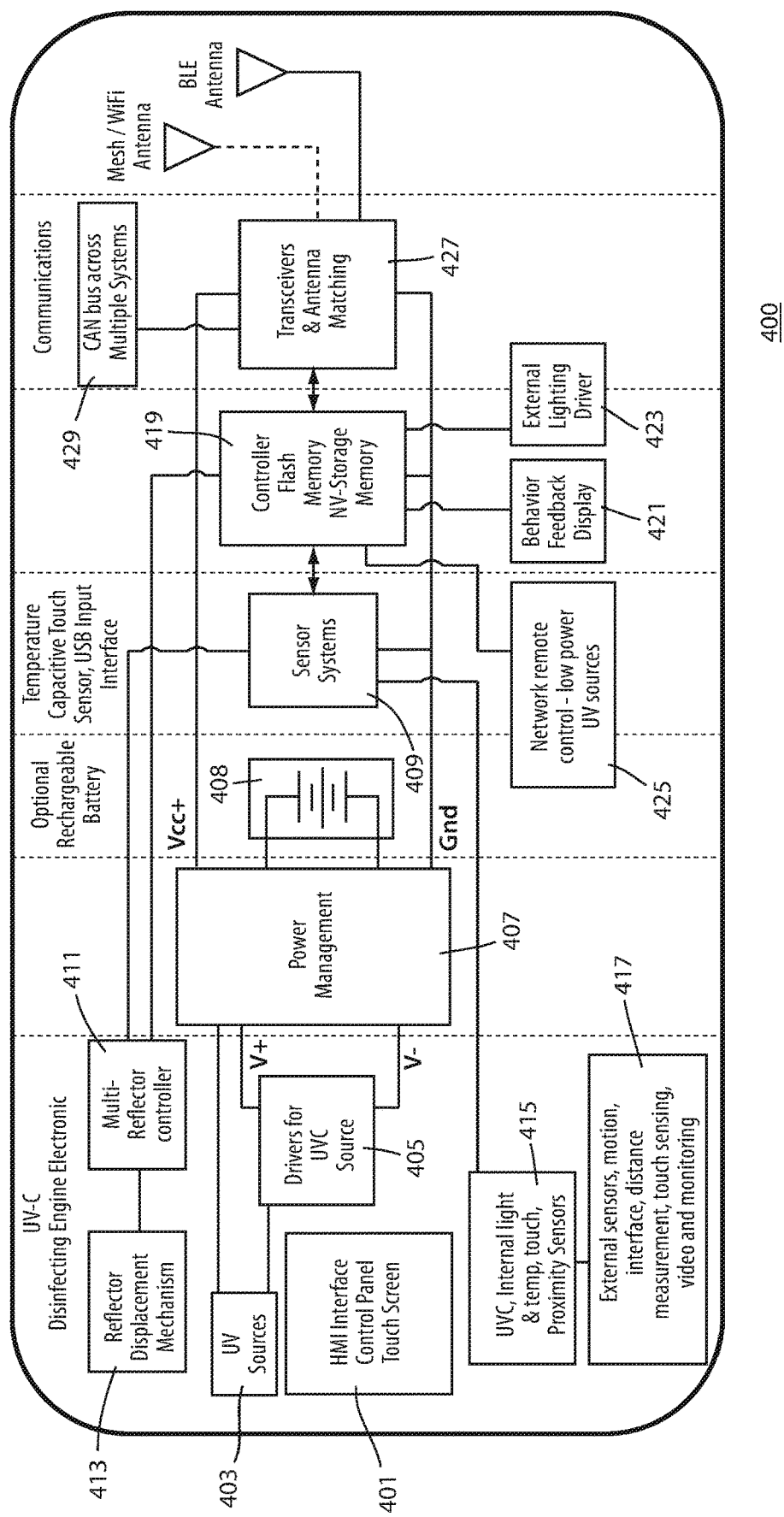
FIG. 4 is a block diagram illustrating the operation of an HMI surface disinfection device in accordance with the invention.

FIG. 4 is a block diagram illustrating the operation of an HMI surface disinfection device in accordance with the invention. FIG. 4 is a block diagram illustrating the operation of an HMI surface disinfection device in accordance with the invention. As seen in FIG. 4, the HMI control system 400 for controlling the HMI control panel 401 includes a plurality of UV sources 403 which are driven by one or more UV-C source drivers 405. Those skilled in the art will recognize that the UV light sources 403 may be cold cathode, low pressure Hg or UV-C LED's. The reactor is based flooding specific areas. As described herein, the UV lamp energy is variable and directed to programmed surfaces. The reflective surface control is programmed for variable intensity, distribution using a delivery mechanism. Mechanisms like micro-canti-level, linear motors or the like can be used to control direction and position of the light sources and reflectors. The UV light sources 403 are powered by a power management control 407 that is a power supply 408 that produces a regulated voltage from AC line voltage or a battery power source such as an optional battery. The battery may be size for the desired dose, interval and typical use cycle. Thus, the UV sources can also be used with a ballast or power source having power and UV-C feedback.

The power management control 407 also controls power to a sensor control 409. The sensor system 409 works to detect and control a multi-reflector controller 411 which operates a reflector displacement mechanism 413. As described herein, the reflector displacement mechanism works to control one or more reflectors used to direct the UV-C light to desired locations on the control panel 401— such as a touch screen. Further, the sensor system 409 also works with proximity sensors as well as internal light, temperature and touch sensors 415 to detect what areas of the touch screen are most often used. This allows the control system to determine desired areas of the touch screen where the UV-C light should be directed. Thus, the HMI control system 400 can actively target areas of a touch screen that are most likely or prone to harbor pathogens and/or other undesirable organisms from multiple user contact and high use. The UV sensor will confirm the type of dose and intensity information, and will track that dose over some predetermined time period. The sensor control 409 can also control a non-volatile storage memory 419 that stores all accumulated usage information and dosage data. Those skilled in the art will be also recognize that other types of external sensors can also be used to make this determination. These optional sensors can include but are not limited to motion, interface use, distance measurement, touch sensing and video sensors. Hence, the HMI using the UV delivery system as described herein uses dynamic moveable reflectors and can use direct feedback from HMI environment in order to track touches and events/cycles. As an example, the feedback sensors across the control panels/screens can include passive infra-red sensor (PIR) grids across the surface of the LCD screen with capacitive touch feedback from the screen function to determine use and UV disinfection requirements.

As seen in FIG. 4, the information stored in the memory 419 can be displayed 421 or used for controlling an external lighting driver 423. A remote network control 425 can also use this information for controlling additional low power UV sources 425. Wireless control using a Wi-Fi or Bluetooth is also accomplished using a transceiver and matching network 427. Antennas are optionally routed to outside ambient or external devices using on-board chip type antennas. This information can also be supplied to a CAN bus across multiple HMI control systems 429 using the transceiver 427 or the like. Hence, the dynamic move-ability of the multi-reflector assembly and sensor network monitoring and the HMI for positioning, as well as the known cycles of use etc. together make a more powerful system as compared to each individual system operating alone.

Figure 5A:
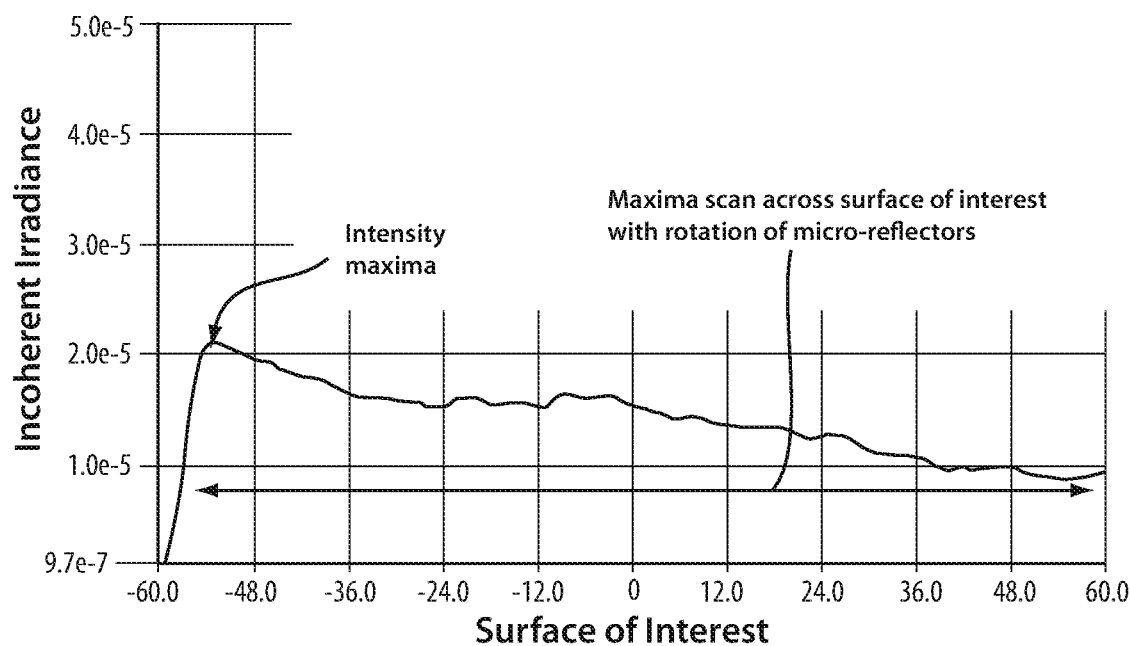
FIG. 5A and FIG. 5B are graphs showing representations of the effects of distributing UV light on a touchscreen surface using micro-reflective surface intensity distribution as described herein.
Figure 5B:
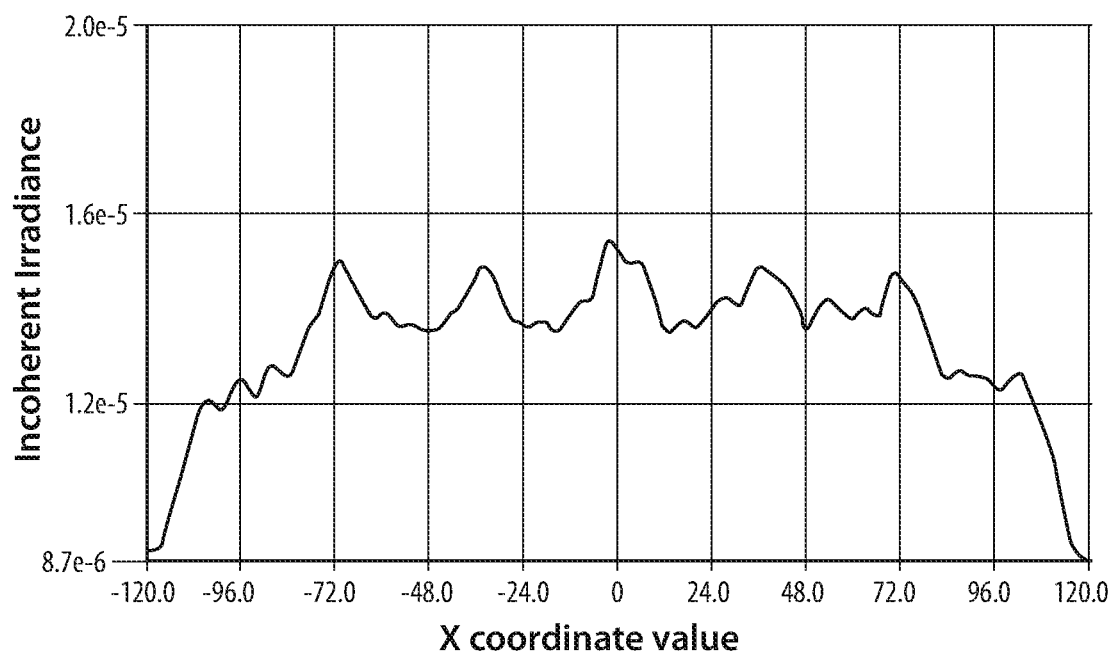

FIG. 5A and FIG. 5B are graphs illustrating the effect of micro-reflective surface intensity and its distribution effects. As seen in FIG. 5A, the intensity maxima of the UV-C light can be controlled so it is greatest or maximized at any particular touchscreen location using the dynamic multi-reflector assembly. FIG. 5B illustrates the resulting scan distribution where the dosage UV-C light is precisely controlled to ensure that the resulting distinction is uniform across the surface of the touchscreen.

Hence, the present invention is directed to multiple embodiments of an HMI such as a control panel, keyboard or the like where a safe and useful dose of ultra-violet C (UV-C) light is applied to the surface of an HMI to provide disinfection of pathogens. Automating the combination of multiple devices with multiple intensities. The need to disinfect a control panel and HMI interfaces and spaces creates a both geometrical problem and a human interface problem. The geometrical problems are centered around available space and light coverage. The available space is often very limited and the coverage can be directed to the most often used areas of the touch screen that need disinfection.

Those skilled in the art, will recognize that the human interface issue relates to the cycle of contact to the touch screen. The occurrence of a human interacting with the interface at an event is counted as an event or "cycle" which will require disinfection when a task using the device is completed. High touch events like touch screen use, Tx key switches, vehicle control interfaces, vitals monitor, order kiosks, ATMs and other devices that are frequency used are high touch devices. In order to disinfect the complete environment, there is a need to disinfect the high touch areas on the control panel/HMI interface, and then the general area between inter-human usage. Automating this process allows disinfection while in normal operating workflow and between users or events.

As described herein, a highly effective solution uses precision lighting delivery control with active and passive control of UV-C having dynamically moveable multi-reflectors. A light distribution system is described herein having various filtering and reflective properties. Both are important as it is necessary to redistribute the UV-C energy effectively and safely around the product. The reflective properties can allow portions of the product to have different reflective properties allowing varied energy to move through and across the touch screen surface. The other benefit of these properties is the occurrence of a light scattering effect that assists in disinfection. Various embodiments of the invention use a multi-reflector configuration that simultaneously works together to change intensities and distribution of UV-C light in the system. This system of reflective surface can adjust intensity of the light to touchscreen usage rates, but also to programmed patterns for example, scanning vs. continuous vs. intermittent use. Disinfection requires providing an effective dose of UV-C radiation to the entire surface of the HMI. Many mounting scenarios preclude the mounting of a UV-C source orthogonally to the HMI's surface due to physical packaging reasons or aesthetic concerns and this solution offers a useful alternative.

The solution provided herein offers control of intensity and distribution of UV-C light for both efficacy and safety. Those skilled in the art will further recognize that registering a series of events are important to automate a process. In one example, user movement can be tracked using an infra-red (IR) sensor where the disinfection light distribution can be controlled by the preprogrammed movement of reflective surfaces. The reflective surfaces control the planar distribution of UV-C light to optimize disinfection as well as minimizing user exposure. This ensures the requirement to maintain the safety of an operator, or anyone in the vicinity of the HMI. The use of UV-C can present a hazard (specifically, the potential to irritate or damage eyes and skin), and therefore excessive exposure must be avoided.

The present invention can also use remote UV-C sensors for confirming a desired UV-C dose. By locating UV sensors in the farthest-reaching areas of the touch scree, the invention works to sense the UV-C intensity by adjusting a UV-C source to the required dose thus sparing materials in the environment additional UV-C exposure.

In another embodiment, light delivery can be adjusted to available multiple HMI screen surface bezel apertures. HMIs, control panels and touch screens, as used in practical applications have differing constraints on available bezel aperture dimensions. The design and ornamental requirements of the bezel can dictate particular solutions that can be used. As described herein, a manual or preprogrammed adjustable dynamic multi-mirror design helps deliver effective disinfection dose, to any size of surface, by the appropriate adjustment of a dynamic multi-reflector.

Finally, analytics of the internal and external data captured can be used to provide insights into the necessary disinfection parameters. The invention also works to provide "value added" data to users by utilizing insights generated from both the analytic effects of sensors and treatment data. These might take the form of a graded dosage due to workload or seasonal patterns detected in data, that could help users of systems to improve efficiency or the reliance on materials that are compatible with UV-C.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

We claim:

1. A control panel having ultraviolet (UV) disinfection comprising:
    a housing for configuring a liquid crystal display (LCD) screen there having touch screen control;
    a least one light source, comprising at least one LED, operating in the UV-C spectrum; and
    a dynamically moveable multi-reflector assembly for directing light from the at least one LED to a designated area of the LCD screen.

2. A control panel as in claim 1, wherein the dynamically moveable multi-reflector assembly comprises:
    a primary reflector partially surrounding the at least one light source for directing light in a first predetermined direction; and
    a secondary reflector configured forward of the at least one light source for directing light in a second predetermined direction.

3. A control panel as in claim 2, wherein the primary reflector is a U-shaped reflector.

4. A control panel as in claim 2, wherein the at least one light source, primary reflector and secondary reflector move to direct UV-C light to a desired location on the LCD screen.

5. A control panel as in claim 2, wherein the primary reflector and secondary reflector are both rotationally and transnationally moveable along an axis for directing UV-C light to a desired location on the LCD screen.

6. A control panel as in claim 2, wherein the primary reflector and secondary reflector are moveable independent of one another.

7. A control panel as in claim 2, wherein the secondary reflector reflects light from the light source to the primary reflector.

8. A control panel human machine interface (HMI) having surface disinfection comprising:
    a housing having a liquid crystal display (LCD) touch screen therein;
    at least one ultraviolet (UV) light source;
    a moveable multi-reflector assembly for directing light from the UV light source; and
    wherein the multi-reflector assembly can both rotate and/or move linearly along an axis for distributing UV light to a designated location on the LCD surface.

9. A control panel HMI as in claim 8, wherein the multi-reflector assembly comprises:
    a primary reflector partially surrounding the at least one light source for directing light in a first predetermined direction; and
    a secondary reflector configured in front of the at least one light source for directing light in a second predetermined direction.

10. A control panel HMI as in claim 9, wherein the primary reflector has a substantially U-shape.

11. A control panel as in claim 9, wherein the primary reflector and secondary reflector are moveable independent of one another.

12. A control panel as in claim 9, wherein the secondary reflector reflects light from the light source to the primary reflector.

13. A control panel as in claim 8 wherein the UV light emits light in the UV-C spectrum.

14. A control panel used in a human machine interface (HMI) for providing ultraviolet (UV) disinfection comprising:
- a housing with a liquid crystal display (LCD) touch screen configured therein;
- at least one light source for emitting light in the UV-C spectrum;
- a primary reflector partially surrounding the at least one light source for directing light in a first predetermined direction; and
- a secondary reflector configured forward of the at least one light source for directing light towards the primary reflector; and
- wherein the primarily reflector and secondary reflector can rotate or move along a linear axis for directing UV-C light to a desired location on the touch screen.

15. A control panel as in claim 14, wherein the primary reflector and secondary reflector are moveable independent of one another.

16. A control panel as in claim 14, wherein the primary reflector is U-shaped.

17. A control panel as in claim 14, wherein the secondary reflector is substantially flat.

18. A control panel as in claim 14 wherein the light source is a light emitting diode (LED).

* * * * *

UNITED STATES PATENT AND TRADEMARK OFFICE
CERTIFICATE OF CORRECTION

PATENT NO. : 11,083,810 B2
APPLICATION NO. : 16/736691
DATED : August 10, 2021
INVENTOR(S) : Umenei et al.

It is certified that error appears in the above-identified patent and that said Letters Patent is hereby corrected as shown below:

On the Title Page

Item (72), under Inventors: Change "Aghuinhue" to --Aghuinyue--.

Signed and Sealed this
Nineteenth Day of October, 2021

Drew Hirshfeld
*Performing the Functions and Duties of the
Under Secretary of Commerce for Intellectual Property and
Director of the United States Patent and Trademark Office*